United States Patent
Nikolenko

(10) Patent No.: US 9,465,089 B2
(45) Date of Patent: Oct. 11, 2016

(54) NMR SPECTROSCOPY DEVICE BASED ON RESONANCE TYPE IMPEDANCE (IR) SENSOR AND METHOD OF NMR SPECTRA ACQUISITION

(71) Applicant: NeoVision LLC, Albany, CA (US)

(72) Inventor: Yury Nikolenko, San Jose, CA (US)

(73) Assignee: NeoVision LLC, Albany, CA (US)

( * ) Notice: Subject to any disclaimer, the term of this patent is extended or adjusted under 35 U.S.C. 154(b) by 717 days.

(21) Appl. No.: 13/690,786

(22) Filed: Nov. 30, 2012

(65) Prior Publication Data

US 2013/0141095 A1    Jun. 6, 2013

Related U.S. Application Data

(60) Provisional application No. 61/565,844, filed on Dec. 1, 2011.

(51) Int. Cl.
| | |
|---|---|
| *G01V 3/00* | (2006.01) |
| *G01R 33/341* | (2006.01) |
| *G01R 33/44* | (2006.01) |

(Continued)

(52) U.S. Cl.
CPC ............. *G01R 33/341* (2013.01); *G01N 24/08* (2013.01); *G01R 33/34053* (2013.01); *G01R 33/383* (2013.01); *G01R 33/3808* (2013.01); *G01R 33/44* (2013.01)

(58) Field of Classification Search
CPC ................ G01R 33/341; G01R 33/44; G01R 33/34053; G01R 33/3808; G01R 33/383; G01N 24/08; G01N 27/023
See application file for complete search history.

(56) References Cited

U.S. PATENT DOCUMENTS

| | | |
|---|---|---|
| 2,583,724 A | 1/1952 | Broding |
| 3,774,103 A | 11/1973 | Laukien |

(Continued)

FOREIGN PATENT DOCUMENTS

| | | |
|---|---|---|
| GB | 1471480 A | 4/1977 |
| SU | 1408391 A1 | 7/1988 |

(Continued)

OTHER PUBLICATIONS

CW Nuclear Magnetic Resonance, available on Jan. 17, 2006 at http://www.physics.rutgers.edu/ugrad/387/nmr.pdf.*
Nuclear Magnetic Resonance, available at http://www.advancedlab.org/mediawiki/index.php/Nuclear_Magnetic_Resonance on Mar. 11, 2012.*

(Continued)

*Primary Examiner* — Daniel Miller
(74) *Attorney, Agent, or Firm* — Pergament & Cepeda LLP; Edward D. Pergament; Milagros A. Cepeda

(57) ABSTRACT

Processes and apparatuses are provided for contactless Nuclear magnetic resonance ("NMR") spectrum acquiring and spectroscopic analysis and/or measuring or monitoring, in-line, in-situ and/or in real time, at least one composition or object under test of one or more solid, liquid, and/or gaseous substances and/or one or more bulk materials. One or more apparatus may include a resonance type impedance sensor having at least two coils, at least one coil of the at least two coils being at least one excitation coil, at least one other coil of the at least two coils being at least one sensing coil. The method(s) involve acquiring an NMR spectrum of an object under test while changing at least one of the frequency of an IR sensor and the intensity of the magnetic field applied to an object under test and/or sweeping intensity of the magnetic field applied to the object under test.

16 Claims, 6 Drawing Sheets

(51) Int. Cl.
  *G01N 24/08* (2006.01)
  *G01R 33/34* (2006.01)
  *G01R 33/38* (2006.01)
  *G01R 33/383* (2006.01)

(56) References Cited

U.S. PATENT DOCUMENTS

| | | |
|---|---|---|
| 4,058,766 A | 11/1977 | Vogel et al. |
| 4,334,604 A | 6/1982 | Davies |
| 4,433,286 A | 2/1984 | Capots |
| 5,003,262 A | 3/1991 | Egner et al. |
| 5,091,704 A | 2/1992 | Kopera |
| 5,132,617 A | 7/1992 | Leach et al. |
| 5,213,655 A | 5/1993 | Leach et al. |
| 5,242,524 A | 9/1993 | Leach et al. |
| 5,343,146 A | 8/1994 | Koch et al. |
| 5,516,399 A | 5/1996 | Balconi-Lamica et al. |
| 5,541,510 A | 7/1996 | Danielson |
| 5,550,478 A | 8/1996 | Kopera |
| 5,559,428 A | 9/1996 | Li et al. |
| 5,644,221 A | 7/1997 | Li et al. |
| 5,659,492 A | 8/1997 | Li et al. |
| 5,660,672 A | 8/1997 | Li et al. |
| 5,663,637 A | 9/1997 | Li et al. |
| 5,731,697 A | 3/1998 | Li et al. |
| 5,770,948 A | 6/1998 | Li et al. |
| 5,889,401 A | 3/1999 | Jourdain et al. |
| 5,942,893 A | 8/1999 | Terpay |
| 6,072,313 A | 6/2000 | Li et al. |
| 6,310,480 B1 | 10/2001 | Cohen et al. |
| 6,377,039 B1 | 4/2002 | Goldfine et al. |
| 6,380,747 B1 | 4/2002 | Goldfine et al. |
| 6,404,197 B1 | 6/2002 | Anderson et al. |
| 6,404,199 B1 | 6/2002 | Fujita et al. |
| 6,407,546 B1 | 6/2002 | Le et al. |
| 6,433,541 B1 | 8/2002 | Lehman et al. |
| 6,448,795 B1 | 9/2002 | Ermakov et al. |
| 6,511,851 B1 | 1/2003 | Payne et al. |
| 6,558,229 B2 | 5/2003 | Kimura et al. |
| 6,563,308 B2 | 5/2003 | Nagano et al. |
| 6,593,738 B2 | 7/2003 | Kesil et al. |
| 6,602,724 B2 | 8/2003 | Redeker et al. |
| 6,621,264 B1 | 9/2003 | Lehman et al. |
| 6,657,433 B1 | 12/2003 | Locatelli et al. |
| 6,663,469 B2 | 12/2003 | Kimura et al. |
| 6,669,557 B2 | 12/2003 | Adams et al. |
| 6,707,540 B1 | 3/2004 | Lehman et al. |
| 6,741,076 B2 | 5/2004 | Le |
| 6,762,604 B2 | 7/2004 | Le |
| 6,815,947 B2 | 11/2004 | Scheiner et al. |
| 6,878,038 B2 | 4/2005 | Johansson et al. |
| 6,891,380 B2 | 5/2005 | Kesil et al. |
| 6,920,399 B2 | 7/2005 | Priev et al. |
| 6,923,711 B2 | 8/2005 | Laursen et al. |
| 6,966,816 B2 | 11/2005 | Swedek et al. |
| 6,975,107 B2 | 12/2005 | Hanawa et al. |
| 6,977,503 B2 | 12/2005 | Prado |
| 7,008,296 B2 | 3/2006 | Swedek et al. |
| 7,008,297 B2 | 3/2006 | Johansson et al. |
| 7,016,795 B2 | 3/2006 | Swedek et al. |
| 7,043,402 B2 | 5/2006 | Phillips et al. |
| 7,046,001 B2 | 5/2006 | Tada et al. |
| 7,070,476 B2 | 7/2006 | Lehman et al. |
| 7,074,109 B1 | 7/2006 | Bennett et al. |
| 7,078,894 B2 | 7/2006 | Tada et al. |
| 7,095,230 B2 | 8/2006 | Blumich et al. |
| 7,135,870 B2 | 11/2006 | Mohajer et al. |
| 7,195,536 B2 | 3/2007 | Swedek et al. |
| 7,198,545 B1 | 4/2007 | Korovin et al. |
| 7,219,024 B2 | 5/2007 | Gamache et al. |
| 7,247,080 B1 | 7/2007 | Bennett et al. |
| 7,332,902 B1 | 2/2008 | Vermeire et al. |
| 7,352,186 B2 | 4/2008 | Hasegawa et al. |
| 7,374,477 B2 | 5/2008 | Birang et al. |
| 7,500,901 B2 | 3/2009 | Swedek et al. |
| 7,508,201 B2 | 3/2009 | Tada et al. |
| 7,514,938 B2 | 4/2009 | Publicover et al. |
| 7,591,708 B2 | 9/2009 | Birang et al. |
| 7,619,414 B2 | 11/2009 | Yamamoto et al. |
| 7,635,331 B2 | 12/2009 | Kim et al. |
| 7,659,731 B2 | 2/2010 | Lin et al. |
| 7,682,221 B2 | 3/2010 | Swedek et al. |
| 7,714,572 B2 | 5/2010 | Tada et al. |
| 7,737,038 B2 | 6/2010 | Lee et al. |
| 7,795,866 B2 | 9/2010 | Fujita |
| 7,822,500 B2 | 10/2010 | Kobayashi et al. |
| 7,836,756 B2 | 11/2010 | Boudaoud et al. |
| 7,912,661 B2 | 3/2011 | Zeng et al. |
| 8,106,657 B2 | 1/2012 | Sakellariou et al. |
| 8,547,110 B2 | 10/2013 | Kesil et al. |
| 2003/0181827 A1 | 9/2003 | Hojeibane et al. |
| 2005/0156604 A1 | 7/2005 | Red'ko et al. |
| 2007/0103150 A1 | 5/2007 | Tada et al. |
| 2008/0143345 A1 | 6/2008 | Boudaoud et al. |
| 2008/0199359 A1 | 8/2008 | Davis et al. |
| 2009/0027070 A1 | 1/2009 | Gelling |
| 2009/0061733 A1 | 3/2009 | Fujita et al. |
| 2009/0079424 A1 | 3/2009 | Tralshawala et al. |
| 2009/0128272 A1 | 5/2009 | Hills |
| 2009/0132174 A1 | 5/2009 | Burke et al. |
| 2010/0253371 A1 | 10/2010 | Bierl et al. |
| 2010/0327884 A1 | 12/2010 | McCall et al. |
| 2011/0068807 A1 | 3/2011 | Kesil et al. |
| 2011/0114920 A1* | 5/2011 | Roshen et al. ............... 257/31 |
| 2012/0293188 A1 | 11/2012 | Nikolenko et al. |
| 2013/0141117 A1 | 6/2013 | Nikolenko |

FOREIGN PATENT DOCUMENTS

| | | |
|---|---|---|
| WO | 2008076453 A1 | 6/2008 |
| WO | 2008145188 A1 | 12/2008 |
| WO | 2011038003 A1 | 3/2011 |

OTHER PUBLICATIONS

International Search Report and Written Opinion for PCT/US2010/049824, dated Feb. 10, 2011.
B. Jeanneret, J. L. Gavilano, G. A. Racince, CH. Leemann and P. Martinoli: "Inductive conductance measurements in two-dimensional superconducting systems", Applied Physics Letters, vol. 55, No. 22, pp. 2336-2338, dated Nov. 27, 1989.
Notification Concerning Transmittal of International Preliminary Report on Patentability—Chapter I of the Patent Cooperation Treaty, dated Apr. 5, 2012, for International Pat. App. No. PCT/US2010/049824.
International Preliminary Report on Patentability, dated Mar. 27, 2012.
Written Opinion of the International Searching Authority for International Pat. App. No. PCT/US2010/049824.
Notification of Transmittal of the International Search Report and Written Opinion for PCT/US2012/038369, dated Nov. 6, 2012.
The International Search Report for PCT/US2012/038369.
Written Opinion for PCT/US2012/038369.
Office Action for U.S. Appl. No. 12/887,887, dated Mar. 1, 2013.
Restriction Requirement for U.S. Appl. No. 12/887,887, dated Jan. 8, 2013.
Notice of Allowance and Fee(s) Due for U.S. Appl. No. 12/887,887, dated May 28, 2013.
Supplemental Notice of Allowability for U.S. Appl. No. 12/887,887, dated Jun. 20, 2013.
Supplemental Notice of Allowability for U.S. Appl. No. 12/887,887, dated Jun. 25, 2013.
Response to After Allowance Amendment for U.S. Appl. No. 12/887,887, dated Jul. 26, 2013.
Notification of Transmittal of the International Preliminary Report on Patentability, dated Nov. 19, 2013, for International Pat. App. No. PCT/US2012/038369, notification mailed on Nov. 28, 2013.
International Preliminary Report on Patentability for International Pat. App. No. PCT/US2012/038369 and attached Written Opinion of the International Searching Authority for International Pat. App. No. PCT/US2012/038369, report dated Nov. 19, 2013.

* cited by examiner

NMR SPECTROSCOPY DEVICE BASED ON RESONANCE TYPE IMPEDANCE (IR) SENSOR AND METHOD OF NMR SPECTRA ACQUISITION

CROSS-REFERENCE TO RELATED APPLICATION(S)

This application is a non-provisional patent application that claims the benefit of the filing date of, and priority to, U.S. provisional patent application No. 61/565,844, filed Dec. 1, 2011, the entirety of which is incorporated herein by reference.

BACKGROUND OF THE INVENTION

This invention relates to the field of nuclear magnetic resonance (NMR) spectroscopy devices, and more particularly to one or more small scale NMR spectroscopic apparatuses and methods of using same.

Nuclear magnetic resonance, or NMR as it is abbreviated by scientists, is a phenomenon which occurs when the nuclei of certain atoms are immersed in a static magnetic field and exposed to a second oscillating magnetic field. Some nuclei experience this phenomenon, and others do not, dependent upon whether they possess a property called spin. NMR is based on the nuclear magnetic properties of certain elements and isotopes of those elements. It is a fundamental law of quantum mechanics that nuclei with nonzero spin will have a magnetic dipole and will thus interact with electromagnetic radiation. The presence or absence of a spin and the nature of the spin is expressed in terms of the spin quantum number (I) of the nucleus, which may be either 0, ½, or integer multiples of ½. In a uniform magnetic field, a nucleus having a spin quantum number of ½ may assume two orientations relative to the applied magnetic field. The two orientations have different energies, so that it is possible to induce a nuclear transition by applying electromagnetic radiation of the appropriate frequency. This nuclear transition, known as resonance, is thus brought on when the correct combination of magnetic field strength and exciting frequency characteristic of the nuclei of interest are applied.

Spectroscopy is the study of the interaction of electromagnetic radiation with matter. Nuclear magnetic resonance spectroscopy is the use of the NMR phenomenon to study physical, chemical, and biological properties of matter. NMR spectroscopy is one of the principal techniques used to obtain physical, chemical, electronic and/or structural information about molecules due to at least one of the chemical shift, the Zeeman effect, and the Knight shift effect on the resonant frequencies of the nuclei present in the sample. It is a powerful technique that can provide detailed information on the topology, dynamics and/or three-dimensional structure of molecules in one or more liquid and/or gaseous solution(s) and a solid state thereof. Over the past fifty years, NMR spectroscopy has become the preeminent technique that can be used for structural and/or quantitative analysis of a compound in a mixture, especially an organic one. Of all the spectroscopic methods, NMR spectroscopy is the only one for which a complete analysis and interpretation of the entire spectrum is normally expected. Although larger amounts of a sample are needed than for mass spectroscopy, NMR spectroscopy is non-destructive, and with modern instruments, good data may be obtained from samples weighing less than a milligram. One of the most important groups analytically has a nuclear spin quantum number of ½ because the group includes $^1H$ presented in one or many compounds of interest. Because all nuclei have unique resonances, e.g., approximately 100 megahertz in a 2.35 Tesla field for protons, $^1H$ NMR will only detect compounds having protons. Moreover, because the exact frequency at which a proton resonates within this range is related to its chemical environment, the $^1H$ NMR signal of protons of one compound can generally be distinguished from another, and an integrated intensity of the signal is directly proportional to the amount of the compound of interest. The position of the resonance signal is characterized by its frequency, i.e., the chemical shift, which is usually expressed on a ppm scale relative to the resonance frequency of some standard compound.

SUMMARY OF THE INVENTION

The invention relates to electrical devices and, more particularly, to one or more NMR apparatuses, and methods of using same, including method(s) for the NMR spectra acquisition and/or measuring or monitoring at least one of in-line, in-situ and in real time, one or more compositions of at least one of a solid substance, a liquid substance, a gaseous substance and one or more bulk materials. One or more embodiments may be relatively small, light weight apparatuses. In accordance with at least one aspect of the present invention, a distinctive feature of the present invention is the use of a resonance type impedance sensor (also called an impedance resonance (IR) sensor) as a sensing element for one or more NMR spectroscopy devices and one or more NMR measuring or monitoring devices. In at least one embodiment, the IR sensor is a multicoil open-core or air-core inductor comprising at least two coils: an excitation coil and a sensing coil. Preferably, the excitation coil is connected to an alternating current source with frequency sweep. Preferably, the sensing coil is connected to a data processing system. In one or more embodiments, the excitation coil propagates an electromagnetic energy into the sensing coil, and the sensing coil, in turn, generates a probing electromagnetic field. An object under test is located in such a way with respect to the sensing coil such that the probing electromagnetic field penetrates the whole object under test or at least its part (e.g., the object under test may be located within a sensing area of the sensing coil, a portion of the object under test may be located within a sensing area of the sensing coil, etc.). Being electromagnetically coupled with the object under test, the sensing coil preferably perceives all influences on the probing electromagnetic field made by the object under test. In at least one embodiment, the sensing coil perceives at least one influence of the object under test on the probing electromagnetic field. In order to use an advantage in sensitivity of the resonant circuit, in at least one embodiment, the sensing coil is brought in (or configured to operate within) resonance condition by using the alternating current source with frequency sweep. The resonance frequency is a function of intrinsic inductance L, capacitance C, and resistance R parameters of the sensing coil and one or more electromagnetic characteristics of the object under test.

In accordance with at least one aspect of the present invention, an apparatus for contactless Nuclear magnetic resonance ("NMR") spectrum acquiring and spectroscopic analysis and/or measuring or monitoring, in-line, in-situ and/or in real time, at least one composition or object under test of one or more solid, liquid, and/or gaseous substances and/or one or more bulk materials, includes: at least one resonance type impedance (IR) sensor which is a multicoil open-core or air-core inductor, said sensor comprising at least two coils, at least one coil of the at least two coils being at least one excitation coil connectable to at least one alternating current source with frequency sweep, at least one other coil of the at least two coils being at least one sensing coil connectable to at least one data processing system, wherein: (i) upon electrical connection to said current source, said at least one excitation coil is capable of propagating an electromagnetic energy to said at least one sensing coil, which is capable of generating a probing electromagnetic field, (ii) said at least one sensing coil is designed in such a way that intrinsic inductance L, capacitance C, and resistance R parameters of said at least one sensing coil are capable of providing resonance conditions for measuring impedance of object under test or at least a portion of said object under test being disposed within a sensing area of said at least one sensing coil at a predetermined frequency range, and (iii) said at least one sensing coil uses only its intrinsic (distributed) capacitance and is not connected to any capacitance means; at least one magnetic system providing a strong homogeneous magnetic field; at least one power supply; at least one radio frequency (RF) sweep generator, the at least one RF sweep generator being electrically connected to at least one said excitation coil; at least one data acquisition block, the at least one data acquisition block being electrically connected to: (i) at least one said excitation coil, (ii) at least one said sensing coil, or (iii) to both said excitation and sensing coils; at least one calculation block; and at least one communication block.

In one or more embodiments, the at least one data acquisition block has high electrical input impedance. Preferably, the least one data acquisition block has electrical input impedance greater than 10MΩ or substantially greater than 10MΩ.

In at least one embodiment, the apparatus may include at least one test fixture for containing samples. The test fixture may be spun to average any magnetic field variations, as well as said test fixture imperfections.

The magnetic system may include at least one of: (i) at least one electromagnet coil connected to at least one controlled power supply capable to control an intensity of the magnetic field applied to the object under test; (ii) at least one means to measure the intensity of the magnetic field applied to the object under test; (iii) at least one electromagnet; (iv) at least one permanent magnet; and (v) at least one magnetic conductor. The electromagnet coil may be located on a magnetic conductor as far as possible from the gap where said object under test is situated in order to reduce and/or minimize distortions of the homogeneous magnetic field made by and/or controlled by said electromagnet coil. The magnetic system may be transformable and/or convertible such that the magnetic system is capable of changing an intensity of the magnetic field applied to the object under test. The at least one magnetic conductor may include a truncated cone section capable of concentrating the magnetic field applied to the object under test.

The at least one resonance type impedance (IR) sensor may include at least two resonance type impedance (IR) sensors designed to acquire an NMR signal from different target nuclei. The at least one magnetic system and the at least one resonance type impedance (IR) sensor are designed to provide one or more single-side NMR measurements.

In accordance with another aspect of the present invention, a method of acquiring an NMR spectrum using the one or more apparatuses of the present invention may include the steps of: placing an object under test into the sensing area of said IR sensor; searching for resonant frequency of said IR sensor; changing the intensity of the magnetic field applied to the object under test by means of the transformable and/or convertible magnetic system; measuring the intensity of the magnetic field applied to the object under test; calculating of Larmor precession frequency; stopping the changing of the intensity of the magnetic field applied to the object under test when the Larmor precession frequency coincides with, substantially matches, or substantially equals said resonant frequency of said IR sensor; and acquiring an NMR spectrum of said object under test while changing the frequency of said IR sensor by means of said RF sweep generator electrically connected to said excitation coil.

In accordance with a further aspect of the present invention, another method of acquiring an NMR spectrum using one or more apparatuses of the present invention may include the steps of: placing an object under test into the sensing area of said IR sensor; searching for resonant frequency of said IR sensor; changing the intensity of the magnetic field applied to the object under test by means of the transformable and/or convertible magnetic system; measuring the intensity of the magnetic field applied to the object under test; calculating of Larmor precession frequency; stopping the changing of the intensity of the magnetic field applied to the object under test when the Larmor precession frequency coincides with, substantially matches, or substantially equals said resonant frequency of said IR sensor; and acquiring an NMR spectrum of said object under test while changing the intensity of the magnetic field applied to the object under test by means of said at least one electromagnet coil connected to the at least one controlled power supply.

In accordance with yet a further aspect of the present invention, another method of acquiring an NMR spectrum using one or more apparatuses of the present invention may include the steps of: placing an object under test into the sensing area of said IR sensor; searching for resonant frequency of said IR sensor; changing the intensity of the magnetic field applied to the object under test by means of said at least one electromagnet coil connected to the at least one controlled power supply; measuring the intensity of the magnetic field applied to the object under test; calculating of Larmor precession frequency; stopping the changing of the intensity of the magnetic field applied to the object under test when the Larmor precession frequency coincides with, substantially matches, or substantially equals said resonant frequency of said IR sensor; and acquiring of an NMR spectrum of said object under test while changing the frequency of said IR sensor by means of said RF sweep generator electrically connected to said excitation coil.

In accordance with an even further aspect of the present invention, another method of acquiring an NMR spectrum using one or more apparatuses of the present invention may include the steps of: placing an object under test into the sensing area of said IR sensor; searching for resonant frequency of said IR sensor; changing the intensity of the magnetic field applied to the object under test by means of said at least one electromagnet coil connected to the at least one controlled power supply; measuring the intensity of the magnetic field applied to the object under test; calculating of Larmor precession frequency; stopping the changing of the intensity of the magnetic field applied to the object under test when the Larmor precession frequency coincides with, substantially matches, or substantially equals said resonant frequency of said IR sensor; and acquiring of an NMR spectrum of said object under test by sweeping intensity of the magnetic field applied to the object under test by means of said at least one electromagnet coil connected to the at least one controlled power supply, the sweeping occurring in a vicinity of the intensity of the magnetic field found in the stopping the changing of the intensity step.

The inventors of the present invention have discovered that the traditional electrical circuit, composed of inductor and capacitor, may be replaced by an inductor alone (i.e., the sensing coil may not be connected to any other capacitance means, and the sensing coil may only use its intrinsic (distributed) capacitance C from inter-turn capacitance of the sensing coil). In particular, the inventors have found that impedance resonance sensor systems without the added capacitance showed a dramatic augmentation of sensitivity.

In order to increase sensitivity, the sensing coil may be connected to a data acquisition block with high electrical input impedance and not connected to any additional capacitive or capacitance means, as contrasted to a regular resonant circuit comprising at least two elements: an inductor and a capacitor. A phenomenon of the increasing sensitivity, observed experimentally, can be logically explained in the following way. In a typical traditional resonant circuit, comprising at least an inductor and a capacitor, at resonant condition an intensive exchange of electromagnetic energy occurs causing an increase of electrical current in inductor and interconnecting wires and, as a consequence, causing loss of stored electromagnetic energy and decreasing sensitivity of a sensor made on the basis of such a circuit. In contrast to the typical traditional resonant circuit, in accordance with at least one aspect of the present invention, in a resonant circuit, comprising an inductor only and connected to a data acquisition block with high electrical input impedance, the electrical current in inductor and interconnecting wires is negligibly low. For example, in a case where a sensing coil is connected to a data acquisition unit with 10 MΩ input impedance and 10V operating range, a value of the electrical current does not exceed 1 µA.

One or more aspects of the present invention also may be employed in conjunction with a suitable IR sensor, including, but not limited to, the IR sensor of co-pending U.S. patent application Ser. No. 12/887,887, Filing Date: Sep. 22, 2010, the entirety of which is incorporated herein by reference.

The one or more NMR devices can be built using one or more different magnetic systems: one magnet systems, two magnet systems, Halbach array systems, etc. The magnets can be permanent ones and/or electromagnets. One of the important merits of the IR sensor in accordance with at least one aspect of the present invention is that the IR sensor may be used not only in regular NMR devices which use a special gap in magnet system for placing a sensor and an object under test, but a flat IR sensor can be successfully used for building of one or more single-sided NMR devices.

In order to acquire an NMR signal, a resonance frequency of a sensing coil electromagnetically coupled with an object under test should coincide with a frequency of the Larmor precession for target nuclei. The coincidence can be achieved either: (i) by specially designing a sensing coil with specified intrinsic LCR parameters which provide resonance condition of measurement for an IR sensor at the Larmor precession frequency defined by a magnetic system; or (ii) by adjusting a magnetic field intensity in accordance with at least one existent sensing coil using a transformable (convertible) magnetic system or using an electromagnet coil connected to a controlled power supply.

BRIEF DESCRIPTION OF THE DRAWINGS

For purposes of illustrating the various aspects of the invention, wherein like numerals indicate like elements, there are shown in the drawings simplified forms that may be employed, it being understood, however, that the invention is not limited by or to the precise arrangements and instrumentalities shown. To assist those of ordinary skill in the relevant art in making and using the subject matter hereof, reference is made to the appended drawings and figures, wherein.

DETAILED DESCRIPTION

The general concept of the preferred embodiment is to position a sensor which is an open core or air core inductor, comprising at least two coils. One of the at least two coils, named an excitation coil, is connected to an alternating current source with frequency sweep and transfers electromagnetic energy from said source to another coil of the at least two coils, named a sensing coil. The sensing coil is placed in close proximity (near, adjacent, etc.) to an object under test, so that the object may be electromagnetically coupled with the sensing coil. By changing a frequency of an alternating current source, the sensing coil coupled with the object under test may be brought into, or configured to operate in, a state of resonance. In resonance condition the sensing coil represents a tank with electromagnetic energy continuously being drained by the object under test and replenished by the excitation coil. Every change in energy dissipation of the object under test (such change happens in NMR condition) changes an amount of electromagnetic energy stored in the sensing coil and consequently changes a resonance amplitude of the sensing coil coupled with the object under test. The amplitude is read by a data acquisition unit.

Figure 1:
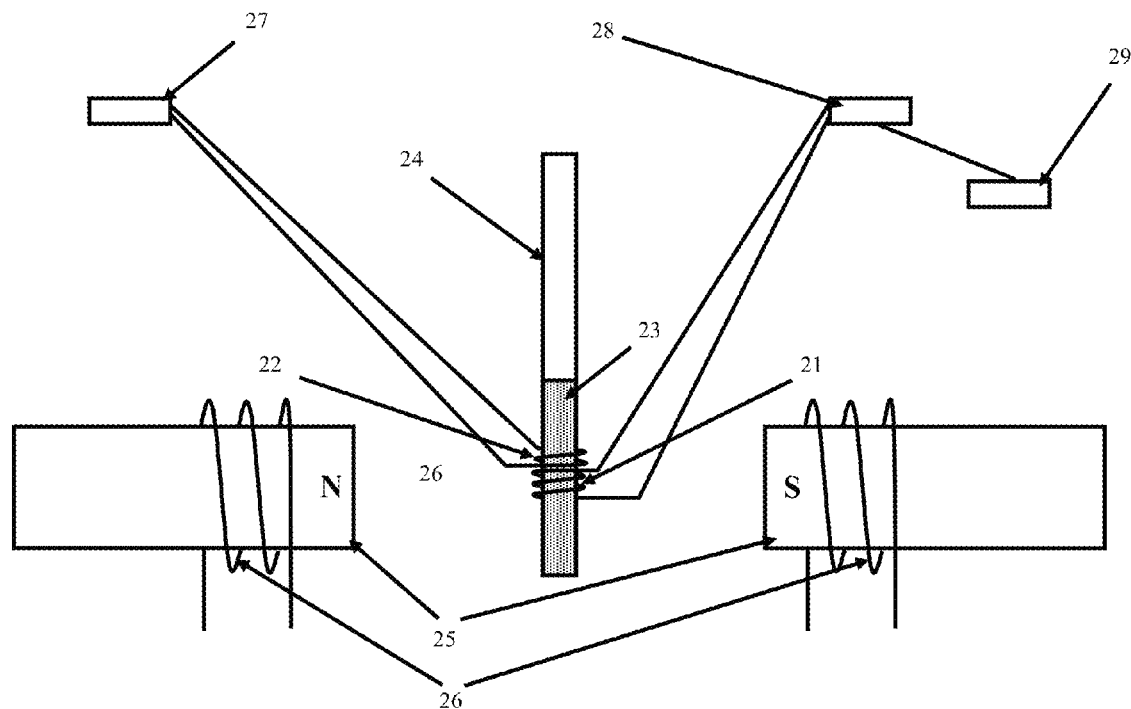
FIG. 1 depicts a schematic of at least one NMR spectroscopy device based on an IR sensor in accordance with at least one aspect of the present invention.

A fundamental distinction of one or more NMR spectroscopes or spectroscopy devices of the present invention, as shown in FIG. 1, is a sensitive or sensing element that is analogous to the one or more Impedance Resonance (IR) sensors disclosed in co-pending applications, including, but not limited to, the IR sensor of co-pending U.S. patent application Ser. No. 12/887,887, Filing Date: Sep. 22, 2010, the entirety of which is incorporated herein by reference, and the IR sensor of co-pending U.S. Provisional Patent Application No. 61/566,267, filed on Dec. 2, 2011, and entitled "Impedance Resonance sensor for real time monitoring of different processes and methods of using same", the entirety of which is incorporated herein by reference.

In accordance with one or more aspects of the present invention, one or more embodiments of the NMR device of present invention comprises:
  a magnetic system for producing a strong homogeneous magnetic field, where the magnetic system comprises of two electromagnets or permanent magnets 25 and two electromagnetic coils 26 for sweeping said strong homogeneous magnetic field,
  a test fixture 24 that is usually spinning for averaging an NMR signal, containing an object under test 23, and
  an IR sensor comprising: at least an excitation coil 22 connected to an RF generator with frequency sweep 27 and at least a sensing coil 21 connected to a processing system comprising: a data acquisition unit 28 and a data storage component 29.

Figure 2:
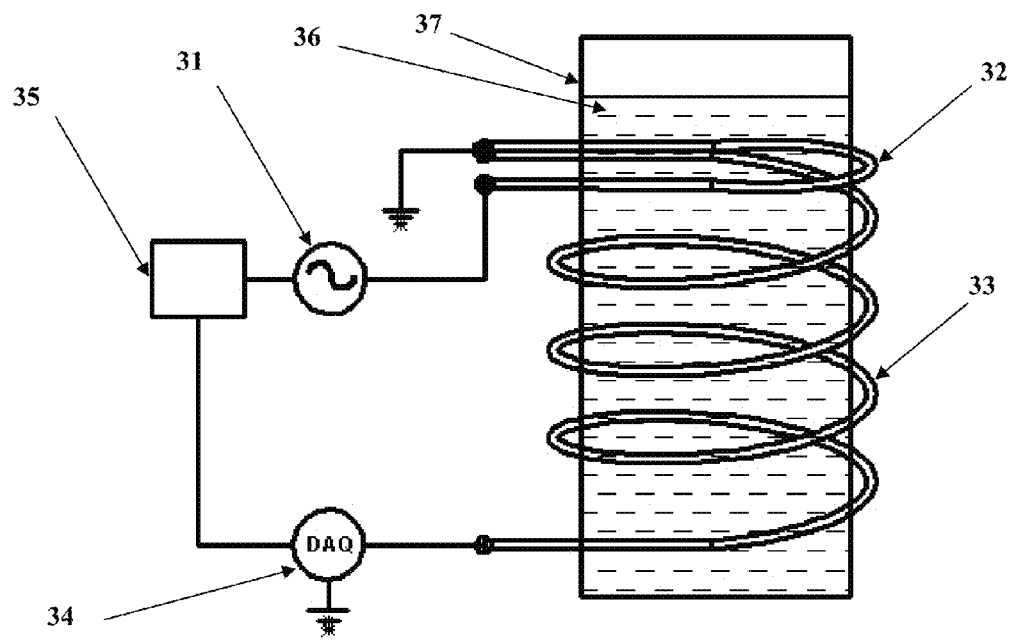
FIG. 2 depicts an embodiment of an IR sensor that may be used in at least one NMR spectroscopy device based on a two magnetic pole or Halbach array design in accordance with at least one aspect of the present invention.

In accordance with at least one aspect of the present invention, one of the embodiments of the IR sensor that may be used with the NMR device is shown in FIG. 2. The embodiment includes at least two coils: an excitation coil 32 and a sensing coil 33. The excitation coil 32 of the at least two coils may include one turn and is connected to a source of harmonic electrical oscillation 31. The excitation coil 32 serves as a "pump" that propagates the sensing coil 33 with electromagnetic energy, and brings said sensing coil 33 into a state of forced electromagnetic oscillations. Owing to the oscillations, the sensing coil 33 emits a harmonious electromagnetic field. In at least one embodiment, the harmonious electromagnetic field is especially intensive in a space encompassed by the sensing coil 33. When the forced oscillations coincide with a natural electromagnetic frequency of the sensing coil 33, the sensing coil 33 begins to oscillate in resonance, and an intensity of the emitted electromagnetic field surges up dramatically. Being in resonance, the sensing coil 33 works like a "tank" that stores electromagnetic energy. Frequency and amplitude of the resonance depends on intrinsic inductance L, capacitance C, and resistance R parameters of the sensing coil 33 and a value of electrical current in the excitation coil 32. After placing a test fixture 36 with an object under test 37 into the sensing coil 33, the electromagnetic field emitted by said sensing coil 33 penetrates the object under test 37 and the test fixture 36. This penetration leads to electromagnetic coupling between the sensing coil 33 and the object under test 37. (In spite of the test fixture 36 being involved in this coupling in one or more embodiments of the present invention, the influence of the test fixture 36 does not change its value from one measurement to another, so the influence is not mentioned further for simplicity of the description.) Due to this electromagnetic coupling between the object under test 37 and the sensing coil 33, the resonance frequency and amplitude of the sensing coil 33 changes their values in comparison with self-resonance values (e.g., for the self-resonance frequency and the amplitude) of the sensing coil 33 itself. In the case of a resonance frequency of a system comprising the sensing coil 33 and the object under test 37 coinciding with the Larmor precession frequency of one or more nuclei contained in the object under test 37, a nuclear-magnetic resonance occurs, and said one or more nuclei, being in a state of NMR, actively absorb electromagnetic energy emitted by the sensing coil 33 and dissipate the electromagnetic energy as heat. This absorption leads to a decreasing quantity of electromagnetic energy stored in the sensing coil 33 and eventually dramatically decreases a voltage that is read by a data acquisition system 34 (best seen in FIG. 2).

From all the information stated above can be drawn the following conclusions. Preferably, for each intensity of the strong magnetic field and for each kind of object under test (such as the object under test 37), the sensing coil 33 is specially designed and produced to be in resonance conditions with the object under test 37 at a Larmor precession frequency of a target nuclei.

Now turning to the features of FIGS. 3-9, several embodiments are shown of NMR spectroscopes based on an IR sensor and different Halbach magnet arrays. The main merit of Halbach magnet arrays in comparison with two magnetic pole systems is that Halbach magnet arrays produce a more homogeneous and stronger magnetic field in greater volume than a magnetic field produced by two magnetic pole systems.

Figure 3:
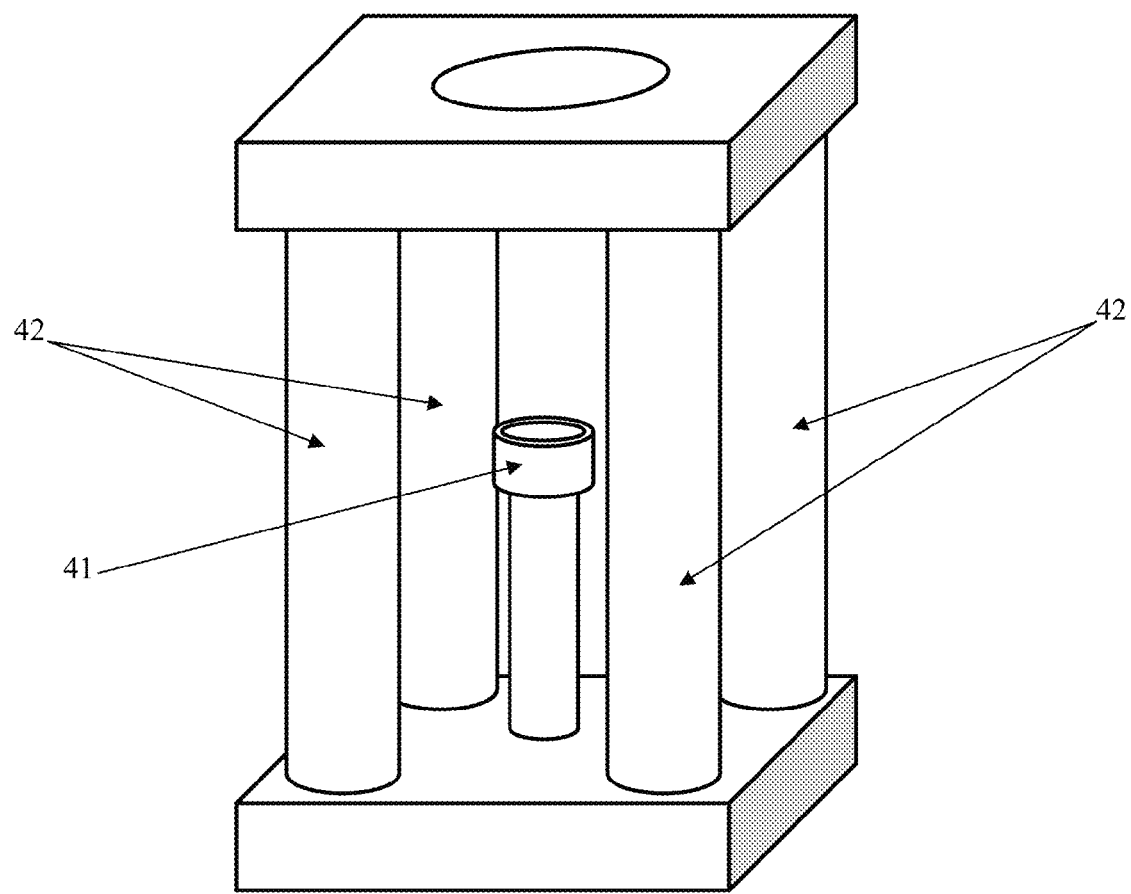
FIG. 3 depicts an embodiment of a low-field, open-access Halbach magnet array NMR spectroscopy device based on an IR-sensor in accordance with at least one aspect of the present invention.
Figure 4:
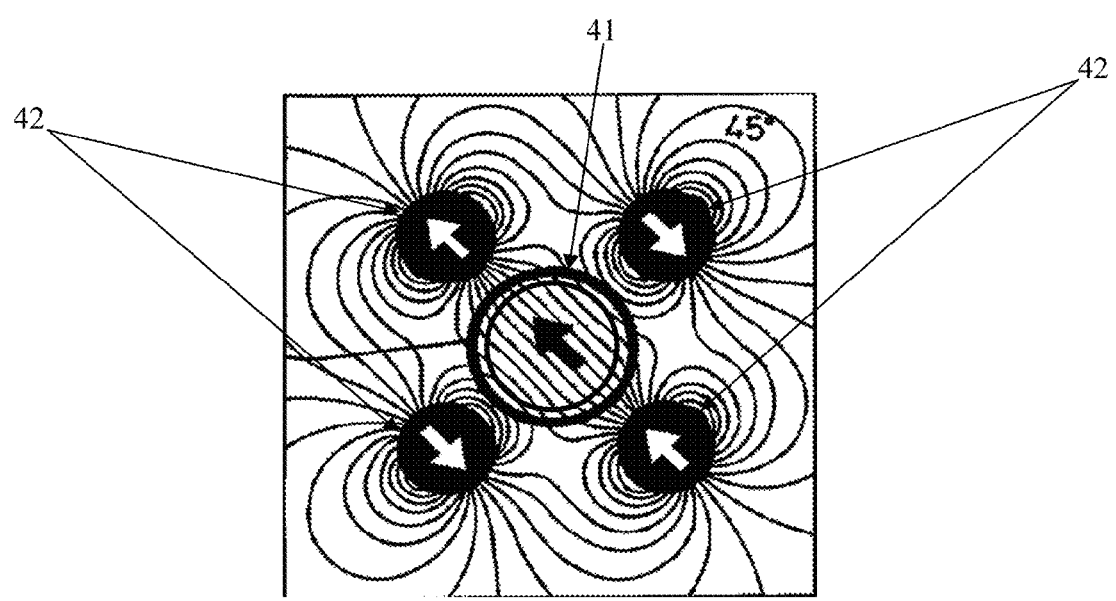
FIG. 4 depicts a magnetic field shape in a cross section of a low-field, open-access Halbach magnet array NMR spectroscopy device based on an IR sensor in accordance with at least one aspect of the present invention.

FIG. 3 shows an open-access NMR spectroscopy device in accordance with at least one aspect of the present invention. The NMR spectroscopy device uses an IR sensor 41 analogous to the IR sensor shown in FIG. 2. Indeed, the IR sensors shown in FIGS. 2-3 may employ one or more of the same or similar components (e.g., the IR sensor 41 may employ the excitation coil 32 and the sensing coil 33), and, therefore, discussion of such components of the IR sensor 41 is not repeated further herein. In addition to such components, a main part of the NMR spectroscopy device are one or more magnets 42. The magnets 42 may be permanent in one or more embodiments. An example of the shape of a strong magnetic field produced by these magnets 42 is shown in FIG. 4. At least one advantage of such NMR spectroscopy devices is comfortable or easy access to an object under test; e.g., an object under test may be easily placed into the IR sensor 41 due to a large enough distance between the magnets 42. The distance is preferably a predetermined distance that may be modified or changed depending on the object(s) under test to be analyzed.

Figure 5:
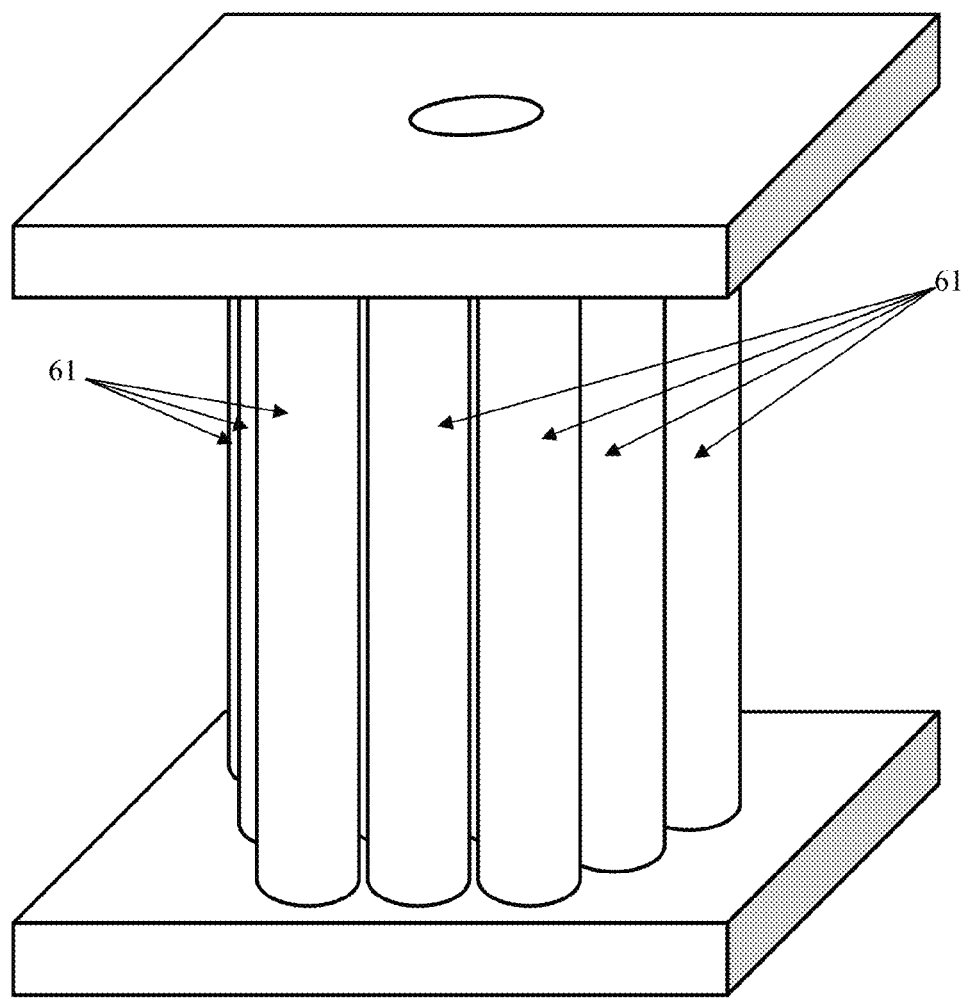
FIG. 5 depicts an embodiment of a strong-field Halbach magnet array NMR spectroscopy device based on an IR sensor in accordance with at least one aspect of the present invention.
Figure 6:
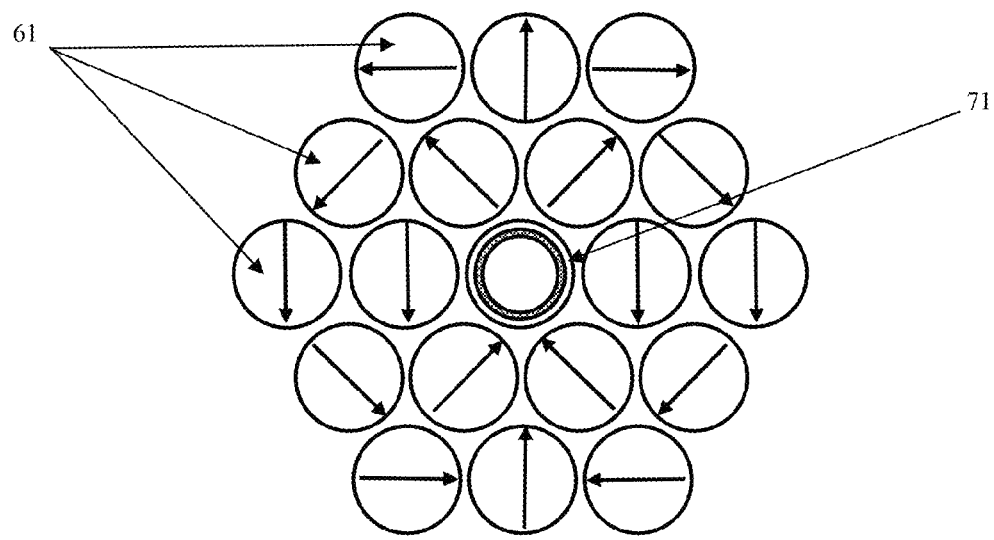
FIG. 6 depicts a cross section of the strong-field Halbach magnet array NMR spectroscopy device based on an IR sensor shown in FIG. 5 in accordance with at least one aspect of the present invention.

In one or more additional embodiments of an NMR spectroscopy device based on an IR sensor, such as the embodiment depicted in FIGS. 5 and 6, a more powerful Halbach magnet array may be used. Preferably, this Halbach array uses additional (i.e., a plurality of magnets 61 that is a larger group than the magnets 42 of the previously discussed embodiment) magnets 61, and one or more directions of magnetization of the magnets 61 may be arranged in a more complex order as shown in FIG. 6. Preferably, the magnets 61 are permanent magnets. As best seen in FIG. 6, an IR sensor 71 is used substantially in, or about near, the middle of the magnets 61. Preferably, the IR sensor 71 is the same as, or similar to, the IR sensor shown in FIG. 2. Indeed, the IR sensor 71 may employ one or more of the same or similar components (e.g., the IR sensor 71 may employ the excitation coil 32 and the sensing coil 33), and, therefore, discussion of such components of the IR sensor 71 is not repeated further herein. Because the group of magnets 61 is larger (relatively to the magnets 42 shown in FIG. 3) and because of the complex order of magnetization of the magnets 61 as discussed above, one or more embodiments of the subject NMR spectroscopy device are more sensitive and accurate than the NMR spectroscopy device shown in FIG. 3.

Figure 7:
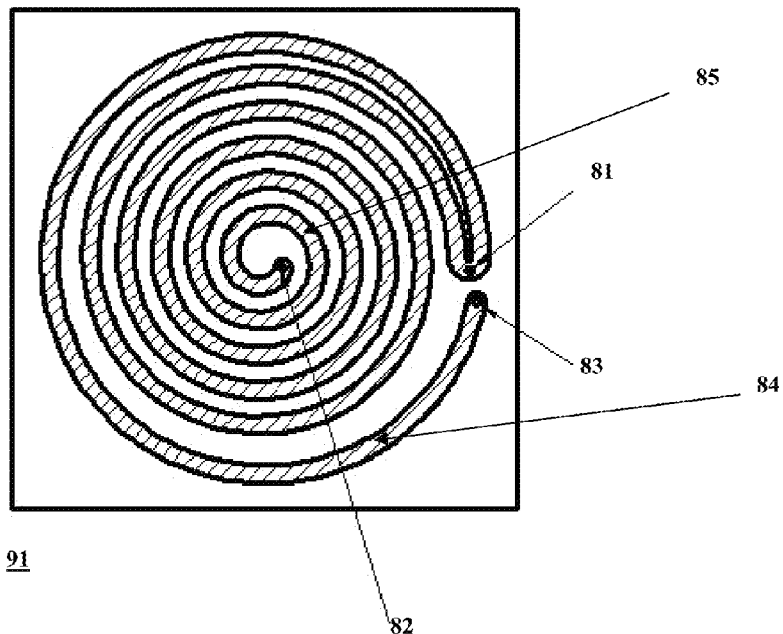
FIG. 7 depicts an embodiment of a flat IR sensor that can be used for one or more single-sided mobile Halbach magnet array NMR spectroscopy devices in accordance with at least one aspect of the present invention.
Figure 8:
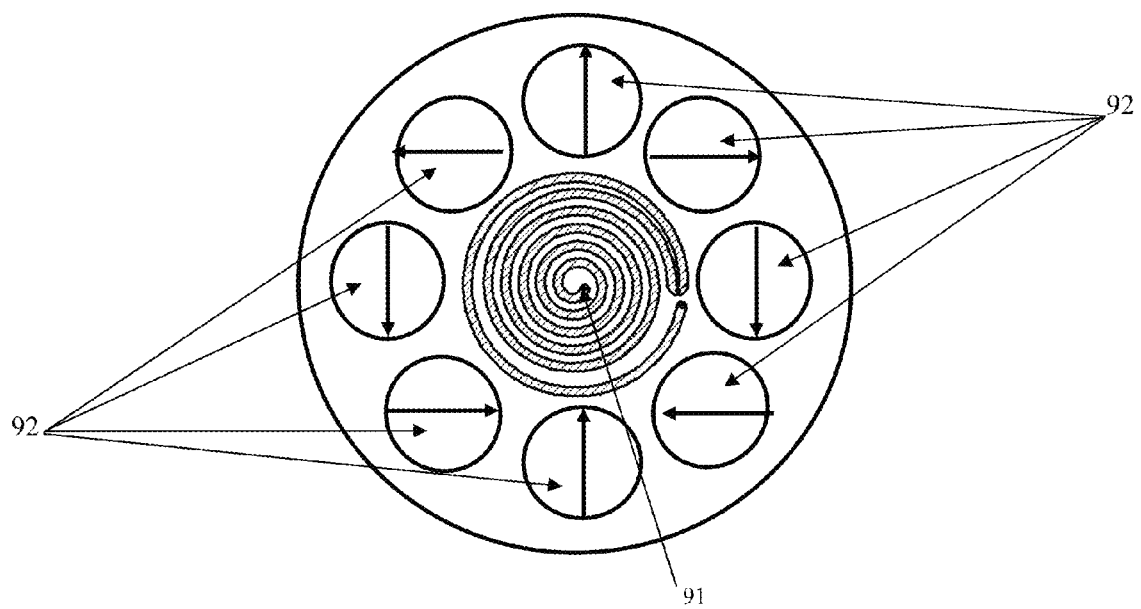
FIG. 8 depicts an embodiment of a single-sided mobile Halbach magnet array NMR spectroscopy device based on a flat IR sensor in accordance with at least one aspect of the present invention.

Another category of an NMR spectroscopy device is or includes NMR surface sensors or single-sided NMR spectroscopy devices. At least one embodiment of possible single-sided NMR spectroscopy devices is shown in FIG. 8. The single-sided NMR spectroscopy device comprises a Halbach array of magnets 92 and an IR sensor 91. Preferably, the magnets 92 are permanent. One example of a flat IR sensor 91 that may be used with the single-sided NMR spectroscopy device is shown in FIG. 7. The flat IR sensor 91 comprises an excitation coil 84 and a sensing coil 85. Preferably, the excitation coil 84 is connected with its contact 83 to an RF generator with frequency sweep, and the sensing coil 85 is connected with its contact 82 to a data acquisition unit. Contact 81 is "ground".

Figure 9:
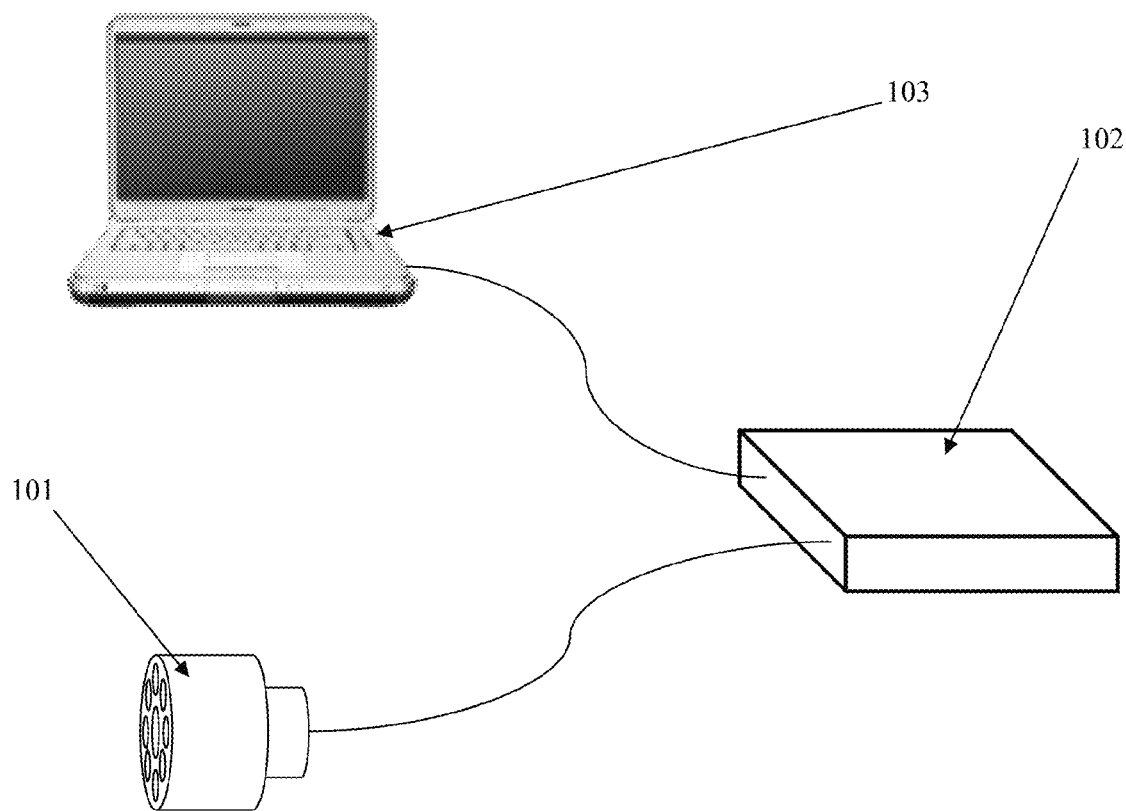
FIG. 9 depicts a system comprising an embodiment of a single-sided mobile Halbach magnet array NMR spectroscopy device based on a flat IR sensor in accordance with at least one aspect of the present invention.

An example of a measurement system that may be used with the present invention shown in FIG. 9 comprises a compact single-sided NMR spectroscopy device 101. Manipulations made with the device 101 during measurements resemble ones made with a computer mouse. A computer-readable storage medium, such as a data acquisition unit 102, used commonly, such as, but not limited to, a hard disk, a flash memory, a CD, a DRAM or the like, an optional combination thereof, a server/database, etc. may be used to cause a processor, such as, but not limited to, the first processor (also referred to as a computer) 103, etc. to perform the steps of the methods disclosed herein, including those steps for analyzing and taking readings from an object under test. The computer-readable storage medium, such as element 102, may be a non-transitory computer-readable medium, and/or the computer-readable medium 102 may comprise all computer-readable media, with the sole exception being a transitory, propagating signal. The computer-readable storage medium 102 may include media that store information for predetermined or limited or short period(s) of time and/or only in the presence of power, such as, but not limited to Random Access Memory (RAM), register memory, processor cache(s), etc.

In accordance with at least one aspect of the present invention, the methods, system, and computer-readable storage medium 102 related to the processors, such as the processor 103, as described above may be achieved utilizing suitable hardware, such as that illustrated in the figures. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The processors, such as the processor 103, may also include and/or be made of one or more microprocessors. Still further, the various aspects of the invention may be implemented by way of software and/or firmware program(s) that may be stored on suitable storage medium 102 (e.g., computer-readable storage medium, hard drive, etc.) or media (such as floppy disk(s), memory chip(s), etc.) for transportability and/or distribution.

Figure 10:
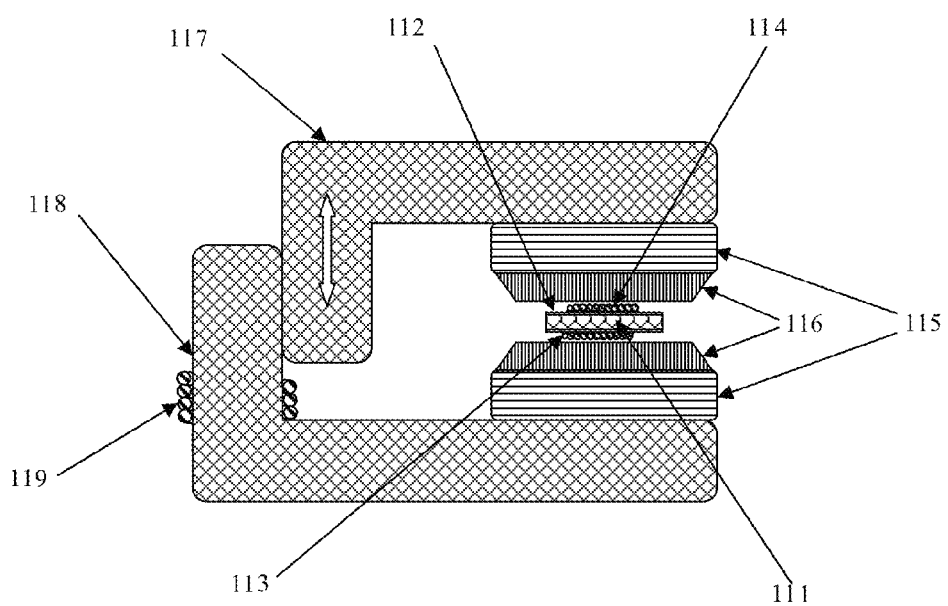
FIG. 10 depicts a schematic of a two permanent magnet NMR spectroscopy device based on an IR sensor in accordance with at least one aspect of the present invention.

FIG. 10 shows a schematic of one of possible embodiments of a two permanent magnet NMR spectroscopy device (also referred to as a spectrometer) based on an IR-sensor with an adjustable gap between magnetic poles. The subject NMR spectroscopy device preferably comprises at least an IR sensor comprising:

An excitation coil 113 connected to an RF sweep generator (not shown),

A sensing coil 114 connected to a data processing system (not shown), a test fixture 112 containing a sample or object under test 111, two permanent magnets 115, truncated cone sections 116, preferably made of at least a magnetic material having high permeability (e.g., where relative permeability $\mu/\mu_o$ is equal or more than 4000) and a high saturation level (e.g., where the saturation level is equal or more than 15000 gauss), an upper movable part of a magnetic conductor 117, preferably made of at least a magnetic material having high permeability (e.g., where relative permeability $\mu/\mu_o$ is equal or more than 4000) and a high saturation level (e.g., where the saturation level is equal or more than 15000 gauss), a lower part of a magnetic conductor 118, preferably made of at least a magnetic material having high permeability (e.g., where relative permeability $\mu/\mu_o$ is equal or more than 4000) and a high saturation level (e.g., where the saturation level is equal or more than 15000 gauss), and an electromagnet coil 119 connected to a controlled power supply (not shown). Even though the RF sweep generator, the data processing system and the controlled power supply are not shown in FIG. 10, any RF sweep generator, data processing system (e.g., items 102 and/or 103 discussed above) and controlled power supply may be used known to those skilled in the art. Examples of the RF sweep generator, data processing system and power supply may also be found in co-pending U.S. patent application Ser. No. 12/887,887, Filing Date: Sep. 22, 2010, the entirety of which is incorporated herein by reference.

Preferably, the NMR spectrometer shown in FIG. 10 is tuned to a specific nucleus ($^1$H, $^{13}$C, or one of many others isotopes that contain an odd number of protons and/or of neutrons having an intrinsic magnetic moment and angular momentum, in other words a nonzero spin). The test fixture 112 including the sample under test 111 is preferably oriented orthogonally to an external magnetic field, substantially between the poles of a powerful magnet comprising of: the two permanent magnets 115, the two truncated cone sections 116, the upper part of magnetic conductor 117, the lower part of magnetic conductor 118, and the electromagnet coil 119 connected to the controlled power supply. RF radiation of an appropriate frequency emitted by the IR sensor penetrates into the sample 111, and the same IR sensor preferably measures a quantity of RF energy absorbed by the sample or object under test 111. Data from the IR sensor may be monitored by a dedicated computer (such as the computer 103 shown in FIG. 9). Preferably, the computer, such as the computer 103, also manages sweeping of the magnetic field by means of the controlled power supply and the electromagnet coil 119.

Adjustment of the Larmor precession frequency for different objects under test may be done by changing the gap between the truncated cones section 116 connected to the permanent magnets 115 using an ability of the magnetic system to be transformed by means of a moving upper part of the magnetic system, the moving upper part comprising:

the upper movable part of magnetic conductor 117, the upper permanent magnet 115, and the upper truncated cone section 116.

Figure 11:
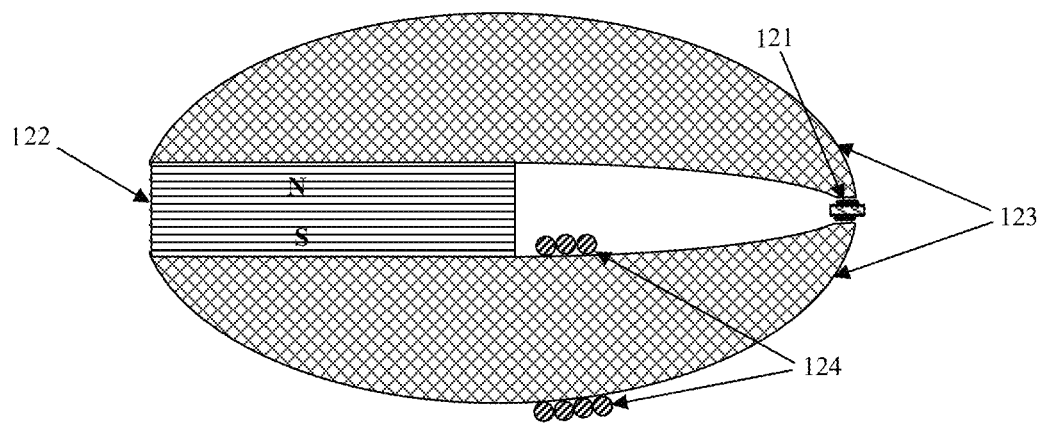
FIG. 11 depicts a schematic of a single permanent magnet NMR spectroscopy device based on an IR sensor in accordance with at least one aspect of the present invention.

Another possible embodiment of an NMR spectroscopy device based on an IR-sensor in accordance with at least one aspect of the present invention is depicted in FIG. 11. The NMR spectroscopy device includes:

an IR sensor 121 with a test fixture containing a sample or object under test connected to a controller (not shown, but the controller may be the same or similar to the test fixture 112 such that no further discussion is made herein).

a permanent magnet 122;

two parts of magnetic conductor preferably made of at least a magnetic material having high permeability (e.g., where relative permeability $\mu/\mu_o$ is equal or more than 4000) and a high saturation level (e.g., where the saturation level is equal or more than 15000 gauss); and an electromagnet coil 124 connected to a controlled power supply (not shown, but again, any controlled power supply known to those skilled in the art may be used as explained above).

A principle of operation of the embodiment shown in FIG. 11 is the same as the embodiment depicted in FIG. 10. Specifically, the shape of the respective magnetic conductor provides a huge concentration of a magnetic field into the gap where the IR sensor containing the sample or the object under test is located. As a result, more sensitive and more accurate readings may be obtained. In one or more alternative embodiments, the shape of the magnetic conductor (such as the two parts 123 shown in FIG. 11 and the two parts 117, 118 shown in FIG. 10) may be changed to a predetermined shape and/or size depending on the sample or object under test to be analyzed.

At least one embodiment of the sensor that pertains to the present application is similar to one disclosed in our pending U.S. patent application Ser. No. 12/887,887, Filing Date: Sep. 22, 2010, the entirety of which is incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. An apparatus for contactless acquiring of a nuclear magnetic resonance (NMR) spectrum of an object under test and analyzing said spectrum in order for (A) detecting (B) measuring or (C) monitoring at least one chemical or biological component of said object under test in real time in-line or in-situ, comprising:

at least one resonance type impedance (IR) sensor which is a multicoil open-core or air-core inductor, said sensor comprising at least two coils, at least one coil of the at least two coils being at least one excitation coil connected to at least one alternating current source with frequency sweep, at least one other coil of the at least two coils being at least one sensing coil connected to at least one data processing system, wherein: (i) upon electrical connection to said current source, said at least one excitation coil is to propagate electromagnetic energy into said at least one sensing coil to generate a probing electromagnetic field at a Larmor frequency of the at least one chemical or biological component, (ii) said at least one sensing coil having intrinsic inductance L, intrinsic capacitance C, and intrinsic resistance R parameters to provide resonance conditions for measuring said probing electromagnetic energy drain from a resonant circuit represented by said sensing coil, caused by energy dissipation due to Larmor precession around an external magnetic field of a magnetic moment of particles of the at least one chemical or biological component of said object under test or at least a portion of said object under test being disposed within a sensing area of said at least one sensing coil at a predetermined frequency range defined by said Larmor frequency, and (iii) said at least one sensing coil uses only its intrinsic capacitance and is not connected to any capacitance means;

at least one magnetic system providing a constant or variable homogeneous magnetic field;

at least one radio frequency (RF) sweep generator, the at least one RF sweep generator being electrically connected to at least one said excitation coil;

at least one data acquisition block, wherein the at least one data acquisition block is electrically connected to: (i) at least one said excitation coil, (ii) at least one said sensing coil, or (iii) to both said excitation and sensing coils;

at least one calculation block connected to said: at least one data acquisition block, at least one magnetic system, and at least one RF sweep generator;

at least one communication block connected to said at least one calculation block and to a computer in order to provide data interchange between said computer and said NMR apparatus; and at least one power supply electrically connected to said: at least one RF sweep generator, at least one calculation block, at least one magnetic system and at least one communication block.

2. The apparatus of claim 1, wherein said at least one data acquisition block has high electrical input impedance.

3. The apparatus of claim 2, wherein said at least one data acquisition block has electrical input impedance greater than 10MΩ or substantially greater than 10MΩ.

4. The apparatus of claim 1, comprising at least one test fixture for containing samples.

5. The apparatus of claim 4, wherein said test fixture is spun to average any magnetic field variations, as well as said test fixture imperfections.

6. The apparatus of claim 1, wherein said magnetic system comprises at least one of:

(i) at least one electromagnet coil connected to at least one controlled power supply capable to control an intensity of the magnetic field applied to the object under test;

(ii) at least one means to measure the intensity of the magnetic field applied to the object under test;

(iii) at least one electromagnet;

(iv) at least one permanent magnet; and (v) at least one magnetic conductor.

7. The apparatus of claim 6, wherein said electromagnet coil is located on a magnetic conductor as far as possible from the gap where said object under test is situated in order to reduce and/or minimize distortions of the homogeneous magnetic field made by and/or controlled by said electromagnet coil.

8. The apparatus of claim 6, wherein said magnetic system is transformable and/or convertible such that the magnetic system is capable of changing an intensity of the magnetic field applied to the object under test.

9. The apparatus of claim 6, wherein said at least one magnetic conductor includes a truncated cone section capable of concentrating the magnetic field applied to the object under test.

10. The apparatus of claim 9, wherein at least one of:
(i) said truncated cone section is made of at least one magnetic material;
(ii) said at least one magnetic material has a high permeability and a high saturation level; and
(iii) said high permeability is where relative permeability $\mu/\mu_o$ is substantially equal or more than about 4000 and said high saturation level is substantially equal or more than about 15000 gauss.

11. The apparatus of claim 6, wherein at least one of:
(i) said at least one magnetic conductor is made of at least one magnetic material;
(ii) said at least one magnetic conductor includes an upper movable part and a lower part, the upper movable part and the lower part comprising the at least one magnetic material;
(iii) said at least one magnetic material has a high permeability and a high saturation level; and
(iv) said high permeability is where relative permeability $\mu/\mu_o$ is substantially equal or more than about 4000 and said high saturation level is substantially equal or more than about 15000 gauss.

12. The apparatus of claim 1, wherein said at least one resonance type impedance (IR) sensor comprises at least two resonance type impedance (IR) sensors designed to acquire an NMR signal from different target nuclei.

13. A method of acquiring an NMR spectrum using the apparatus of claim 8, the method comprising:
placing an object under test into the sensing area of said IR sensor;
searching for resonant frequency of said IR sensor;
changing the intensity of the magnetic field applied to the object under test by means of the transformable and/or convertible magnetic system;
measuring the intensity of the magnetic field applied to the object under test;
calculating of Larmor precession frequency;
stopping the changing of the intensity of the magnetic field applied to the object under test when the Larmor precession frequency coincides with, substantially matches, or substantially equals said resonant frequency of said IR sensor; and
acquiring an NMR spectrum of said object under test while changing the frequency of said IR sensor by means of said RF sweep generator electrically connected to said excitation coil.

14. A method of acquiring an NMR spectrum using the apparatus of claim 8, the method comprising:
placing an object under test into the sensing area of said IR sensor;
searching for resonant frequency of said IR sensor;
changing the intensity of the magnetic field applied to the object under test by means of the transformable and/or convertible magnetic system;
measuring the intensity of the magnetic field applied to the object under test;
calculating of Larmor precession frequency;
stopping the changing of the intensity of the magnetic field applied to the object under test when the Larmor precession frequency coincides with, substantially matches, or substantially equals said resonant frequency of said IR sensor; and
acquiring an NMR spectrum of said object under test while changing the intensity of the magnetic field applied to the object under test by means of said at least one electromagnet coil connected to the at least one controlled power supply.

15. A method of acquiring an NMR spectrum using the apparatus of claim 6, the method comprising:
placing an object under test into the sensing area of said IR sensor;
searching for resonant frequency of said IR sensor;
changing the intensity of the magnetic field applied to the object under test by means of said at least one electromagnet coil connected to the at least one controlled power supply;
measuring the intensity of the magnetic field applied to the object under test;
calculating of Larmor precession frequency;
stopping the changing of the intensity of the magnetic field applied to the object under test when the Larmor precession frequency coincides with, substantially matches, or substantially equals said resonant frequency of said IR sensor; and
acquiring of an NMR spectrum of said object under test while changing the frequency of said IR sensor by means of said RF sweep generator electrically connected to said excitation coil.

16. A method of acquiring an NMR spectrum using the apparatus of claim 6, the method comprising:
placing an object under test into the sensing area of said IR sensor;
searching for resonant frequency of said IR sensor;
changing the intensity of the magnetic field applied to the object under test by means of said at least one electromagnet coil connected to the at least one controlled power supply;
measuring the intensity of the magnetic field applied to the object under test;
calculating of Larmor precession frequency;
stopping the changing of the intensity of the magnetic field applied to the object under test when the Larmor precession frequency coincides with, substantially matches, or substantially equals said resonant frequency of said IR sensor; and
acquiring of an NMR spectrum of said object under test by sweeping intensity of the magnetic field applied to the object under test by means of said at least one electromagnet coil connected to the at least one controlled power supply, the sweeping occurring in a vicinity of the intensity of the magnetic field found in the stopping the changing of the intensity step.

* * * * *